United States Patent
Bastioli et al.

(10) Patent No.: US 10,138,505 B2
(45) Date of Patent: Nov. 27, 2018

(54) PROCESS FOR THE PRODUCTION OF ORGANIC COMPOUNDS FROM PLANT SPECIES

(71) Applicant: Novamont S.p.A., Novara (IT)

(72) Inventors: Catia Bastioli, Novara (IT); Giampietro Borsotti, Novara (IT); Luigi Capuzzi, Novara (IT)

(73) Assignee: Novamont S.p.A., Novara (IT)

( * ) Notice: Subject to any disclaimer, the term of this patent is extended or adjusted under 35 U.S.C. 154(b) by 877 days.

(21) Appl. No.: 14/385,823

(22) PCT Filed: Mar. 20, 2013

(86) PCT No.: PCT/EP2013/055787
§ 371 (c)(1),
(2) Date: Sep. 17, 2014

(87) PCT Pub. No.: WO2013/139839
PCT Pub. Date: Sep. 26, 2013

(65) Prior Publication Data
US 2015/0111258 A1    Apr. 23, 2015

(30) Foreign Application Priority Data
Mar. 20, 2012 (IT) .............................. NO2012A0002

(51) Int. Cl.
*C12P 19/02* (2006.01)
*C12P 19/14* (2006.01)

(52) U.S. Cl.
CPC ............... *C12P 19/02* (2013.01); *C12P 19/14* (2013.01); *C12P 2201/00* (2013.01)

(58) Field of Classification Search
CPC ...................................................... C12P 19/14
See application file for complete search history.

(56) References Cited

U.S. PATENT DOCUMENTS 8,067,214 B2    11/2011    Burke et al.

FOREIGN PATENT DOCUMENTS

| WO | WO 2006/111604 A1 | 10/2006 |
|----|---|---|
| WO | WO 2008/138892 | 11/2008 |
| WO | WO 2011/014894 A2 | 2/2011 |
| WO | WO 2011/061400 A1 | 5/2011 |
| WO | WO 2011/080296 | 7/2011 |
| WO | WO 2011/091044 A1 | 7/2011 |
| WO | WO 2011/133952 A2 | 10/2011 |

OTHER PUBLICATIONS

Qi et al. Ind. Eng. Chem. Res., 2009, 48:7346-7353.*
Haffner et al. Willdenowia, 1999, 29:27-39.*

* cited by examiner

*Primary Examiner* — Bin Shen
(74) *Attorney, Agent, or Firm* — Finnegan, Henderson, Farabow, Garrett & Dunner, LLP

(57) ABSTRACT

This invention relates to a process for the production of fermentable C5-C6 sugars from oleaginous herbaceous plants comprising the steps of: a) mechanically separating the seeds from the above-ground lignocellulose biomass and breaking-up said lignocellulose biomass; b) placing the above-ground lignocellulose biomass in contact with a basic aqueous solution so as to obtain a paste containing from 10 to 50% by weight of the said lignocellulose biomass at temperature of between 10 and 95° C. for a time of between 1 minute and 24 hours; c) separating out the paste obtained in step b) in a solid fraction containing essentially hemicellulose and cellulose; in a liquid fraction containing lignin and extractables; d) subjecting the said solid fraction containing essentially hemicellulose and cellulose to enzyme hydrolysis.

15 Claims, 3 Drawing Sheets

PROCESS FOR THE PRODUCTION OF ORGANIC COMPOUNDS FROM PLANT SPECIES

This is a national stage application under 35 U.S.C. § 371 of International Application No. PCT/EP2013/055787, filed Mar. 20, 2013, and claims priority to Italian Patent Application No. NO2012A000002, filed Mar. 20, 2012, the content of each of which is incorporated herein by reference.

BACKGROUND OF THE INVENTION

This invention relates to a process which can be used to obtain a plurality of organic compounds that can be used as chemical intermediates, using particular oleaginous plant species as raw material.

This process can be used to extract, separate and recover fermentable saccharides from said plant species. Through this process, C5-C6 sugars having a low lignin content, which are particularly suitable for fermentation processes, are obtained from the residual lignocellulose biomass of the oleaginous plant material after the seeds have been removed.

The lignocellulose biomass, which is rich in carbohydrate polymers comprising C5-C6 sugars (hemicellulose and cellulose), is an important renewable source of fermentable saccharides. However, because of its complex structure, in order to facilitate the enzyme hydrolysis of the carbohydrates to simple sugars (monosaccharides), it is necessary to break the chemical bonds between their structural components (cellulose, hemicellulose and lignin). Pre-treatments intended to destroy the external structure formed of lignin and hemicellulose, in addition to reducing the crystallinity and degree of polymerisation of the cellulose itself, and to allow access to the cellulose by hydrolytic enzymes, are therefore commonly used.

These pre-treatments may be of a physical, chemical and/or biological nature. The type of pre-treatment used, together with the nature of the substrate, has an effect on the efficiency of the subsequent enzyme hydrolysis. Generally, the pre-treatments are costly, complex and harsh treatments which can bring about degradation of the lignin and hemicellulose and the consequent formation of toxic by-products, which can inhibit subsequent fermentation stages.

In order to improve utilisation of the lignocellulose biomass, it is therefore necessary to develop a pre-treatment which, depending on the type of biomass used, will preserve the hemicellulose rich in fermentable sugars, will make it possible to utilise the by-products and will limit the formation on inhibitors, at a lower cost and with lower energy consumption.

Pre-treatment with alkali is a chemical pre-treatment which is able to remove lignin, with reduced degradation of the sugars. One example of pre-treatment with alkali is described in Patent Application WO 2011/014894 (Annikki GmbH), in which a lignocellulose material such as wheat straw is subjected to a 24 hour treatment with an aqueous solution containing hydrogen peroxide and a base. This process requires the presence of an organic solvent to limit dissolution of the hemicellulose and has the disadvantage that it requires long times and high concentrations of bases, which are removed in the form of salts.

Pre-treatment with alkali has also been combined with physical systems of a mechanical or thermal type, for example extrusion treatments, but with appreciable difficulties associated with the low plasticity and poor flow properties of the biomass. However, for good efficiency these treatments require high temperatures and high concentrations of bases and the use of gelling agents to modify the rheological behaviour of the biomass. Through the process according to the invention, using the above-ground lignocellulose biomass derived from the cultivation of oleaginous herbaceous plants, it is possible to obtain C5-C6 sugars with a high sugar yield through pre-treatment with alkali such as extraction with aqueous solutions at a basic pH, at low temperature and without the need to add additives which modify the rheological behaviour of the biomass. Pre-treatment of the biomass in the process according to the invention in fact makes it possible to effectively remove lignin, acetate, extractables and ash at lower temperatures than in known types of pre-treatment, ensuring a high recovery of hemicellulose and cellulose and avoiding the formation of degradation products having an inhibiting effect such as furfural, hydroxymethylfurfural (HMF) and their derivatives. Also, in comparison with the pre-treatment described above, it requires short times and results in a lower consumption of bases and liquids.

DISCLOSURE OF THE INVENTION

This invention relates to a process for the production of fermentable C5-C6 sugars from oleaginous herbaceous plants, the said process comprising the steps of:
a) mechanically separating the seeds from the above-ground lignocellulose biomass of the oleaginous herbaceous plants and comminuting said lignocellulose biomass, reducing it to pieces preferably having a size less than 5 cm, more preferably less than 2 cm, especially preferably 0.5 to 10 mm;
b) bringing the comminuted lignocellulose biomass into contact with a basic aqueous solution in order to prepare an aqueous paste containing the comminuted lignocellulose biomass in an amount of 10 to 50% by weight, at a temperature of between 10 and 95° C., preferably between 25 and 95° C., more preferably 40 and 90° C. and for a time of between 1 minute and 24 hours, preferably between 2 minutes and 10 hours;
c) separating the paste into a solid fraction and a liquid fraction;
d) subjecting the solid fraction to enzyme hydrolysis of the hemicellulose and cellulose contained therein.

DETAILED DESCRIPTION OF THE INVENTION

Figure 1:
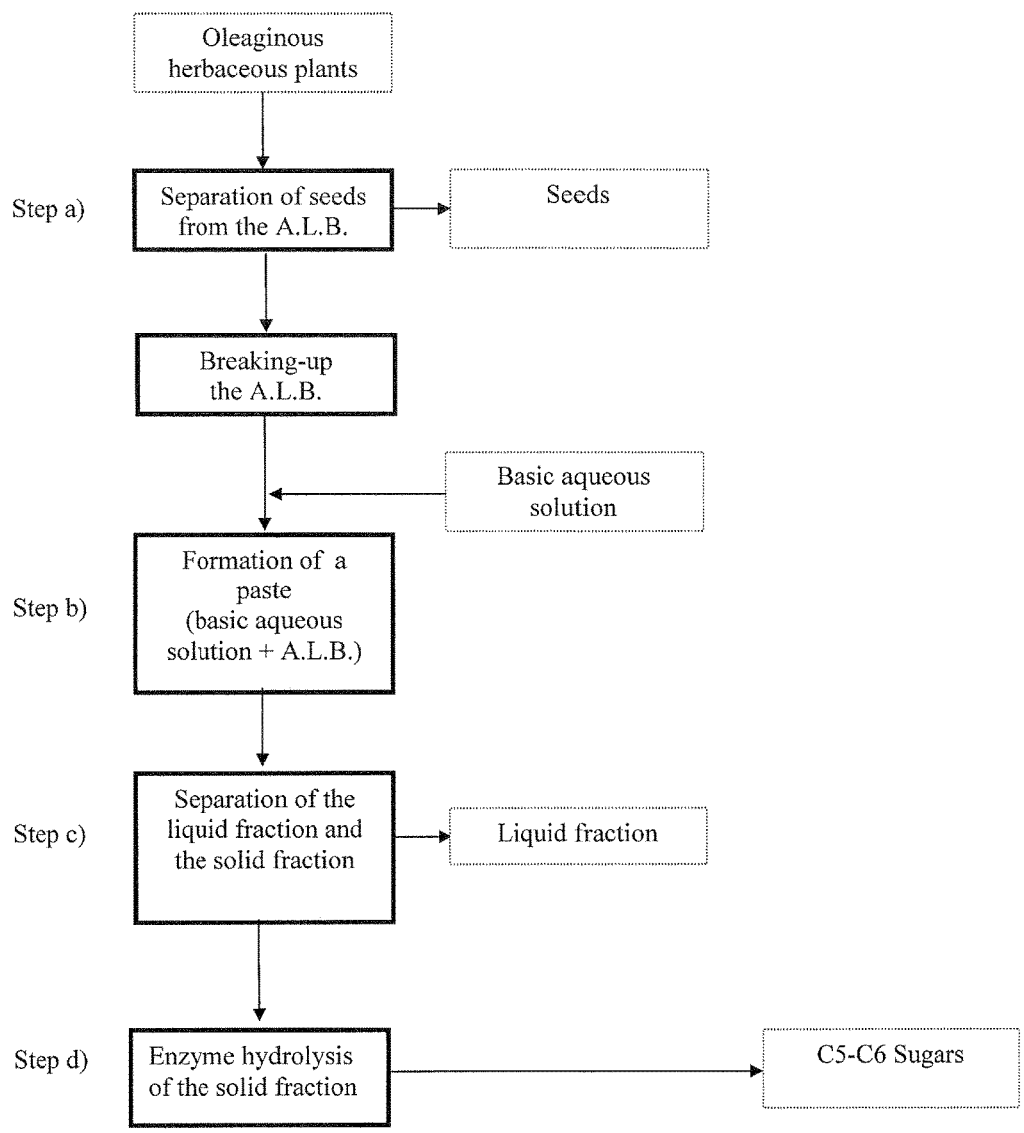
FIG. 1 is a flow diagram of the process of the present invention.

FIG. 1 is a flow diagram showing the process for the production of C5-C6 fermentable sugars from oleaginous herbaceous plants according to the present invention.

Examples of preferable oleaginous plants belong to the Asteraceae family, in particular the tribe Cardueae, preferably the species *Cynara cardunculus* or *Silybum marianum*. Even more preferably *Cynara cardunculus* is used. The oleaginous seed content typically is at least 3% with respect to the dry weight of the above-ground lignocellulose biomass.

In order to obtain higher quantities of fermentable C5-C6 sugars, the oleaginous herbaceous plants are preferably selected from those having a content of not more than 20% by weight of lignin with respect to the dry weight of the above-ground lignocellulose biomass. In such a case, in stage c) of the said process, the paste obtained in stage b) is separated in a solid fraction containing essentially hemicellulose and cellulose and having a lignin content of not more than 10% with respect to the dry weight of the solid fraction and in a liquid fraction containing lignin and extractables having a hemicellulose content of not more than 25% by weight, preferably not more than 10% by weight, with respect to the hemicellulose content of the lignocellulose biomass.

The C5-C6 sugars obtained in step d) have a reduced lignin and inhibitors content and thus are particularly suitable for fermentation processes and require simple operations for separating and purifying products after fermentation.

The term "above-ground lignocellulose biomass" (A.L.B.) refers to the epigeal fraction of the plant which can be obtained after harvesting, comprising the stem or stock with its corresponding branches, leaves and the part of the head remaining after removal of the seeds.

The term "paste" refers the material comprising the basic aqueous solution and the above-ground lignocellulose biomass, which is fed to the device in step c) in order to separate it into a solid and a liquid phase.

The plant species used as a raw material for this invention are cultivated for the production of oleaginous seeds and lignocellulose biomass. The plant species are preferably characterised by a low lignin content. In particular, the invention preferably relates to crops of plant species belonging to the Asteraceae family, in particular the tribe Cardueae, preferably the species *Cynara cardunculus* or *Silybum marianum*. Even more preferably *Cynara cardunculus* is used. These plant species can be grown even in arid areas with a poorly favourable climate. Among these, crops of plant species in which lignin represents not more than 20% by weight of the biomass, more preferably not more than 18% and even more preferably not more than 15% and in which the seeds represent preferably at least 3% of the dry weight of the above-ground biomass, more preferably at least 5% and still more preferably at least 10% are preferable. More preferably, plant species in which the seeds represent at least 10% and in which a fraction of the plant not less than 40% with respect to all the other components of the A.L.B., excluding the seeds, has a lignin content of not more than 15% by weight are used as raw material.

The lignin content of the A.L.B. is determined by summing the quantity of lignin insoluble in acid according to the Tappi T222 method and the quantity of lignin soluble in acid, in turn determined by spectrophotometry through measuring the absorption of ultraviolet radiation at a wavelength of 205 nm.

The process according to the invention will now be described in greater detail. Advantageously, the seeds are separated from the above-ground lignocellulose biomass (step a) in the process) at the time of harvesting.

According to a preferred aspect of this invention, the seeds are subjected to processing to extract the oil, which can be used (directly or after selective hydrogenation treatment to maximise the content of monounsaturated fatty acids) for the production of biofuels and for the production of chemical intermediates such as carboxylic acids and their derivatives. The solid residue from pressing (cake) may be used for the production of animal feedstuffs. The cellulose part of the cake may also be treated to obtain sugars.

In the case in which the seed is subjected to processing for the extraction of oil, this is advantageously performed mechanically or using chemical solvents (e.g. hexane, benzene, toluene), possibly in the presence of enzymes, and may be followed by subsequent refining through physical, chemical or enzyme treatments.

If oleaginous crops having a high oleic acid content are used as the raw material, the oil obtained can be subjected to chemical and/or fermentation treatments to recover derivatives comprising monofunctional or difunctional carboxylic acids from it. Preferably, the oil is subjected to continuous or discontinuous oxidative scission processes as described in Patent Applications WO 2008/138892 and WO 2011/080296. An alternative comprises subjecting the oil or its derivative (acid or methyl ester) to omega-oxidation processes by a fermentation route, possibly followed by hydrogenation reactions.

In both cases the bifunctional derivatives obtained can be used as monomers for the synthesis of polymers.

After the seeds have been separated from the plant, the residual above-ground lignocellulose biomass is subjected to preparatory treatments in order to increase the available surface area of the biomass, to reduce it to small pieces, and to eliminate undesirable components.

Advantageously, the above ground biomass has a water content less than 20% by weight, preferably less than 15% by weight, and is friable, in order to facilitate the reduction of the above ground biomass into fine pieces.

Preferably at the time of harvesting, after the separation of the seeds, the biomass is broken-up and reduced in pieces, preferably having a size of less than 5 cm, more preferably less than 2 cm, especially preferably about 0.5 to 10 mm. The breaking-up (comminution) of the biomass is carried out through mechanical treatments such as grinding, cutting, cracking, mincing or their combinations, and can be performed either dry or in presence of water.

After the comminution of the biomass in step a), it is also possible to carry out an optional washing treatment with water for removing from the biomass salts, acetic acid and other possible components soluble in water. This treatment allows to reduce the amount of base necessary in step b) of the process.

The washing step is preferably carried out at a temperature comprised between 25 and 100° C. Depending on the weight percentage of the solid biomass with respect to the water, the separation of the solid from the aqueous phase can be effected:

with a mechanical press for a solid content between 15-50% by weight;

by filtration in reactor for a solid content lower than 15% by weight.

The removed aqueous washing solution may be reused several times and the water may be recovered at the end of the washing for the subsequent treatments.

Figure 2:
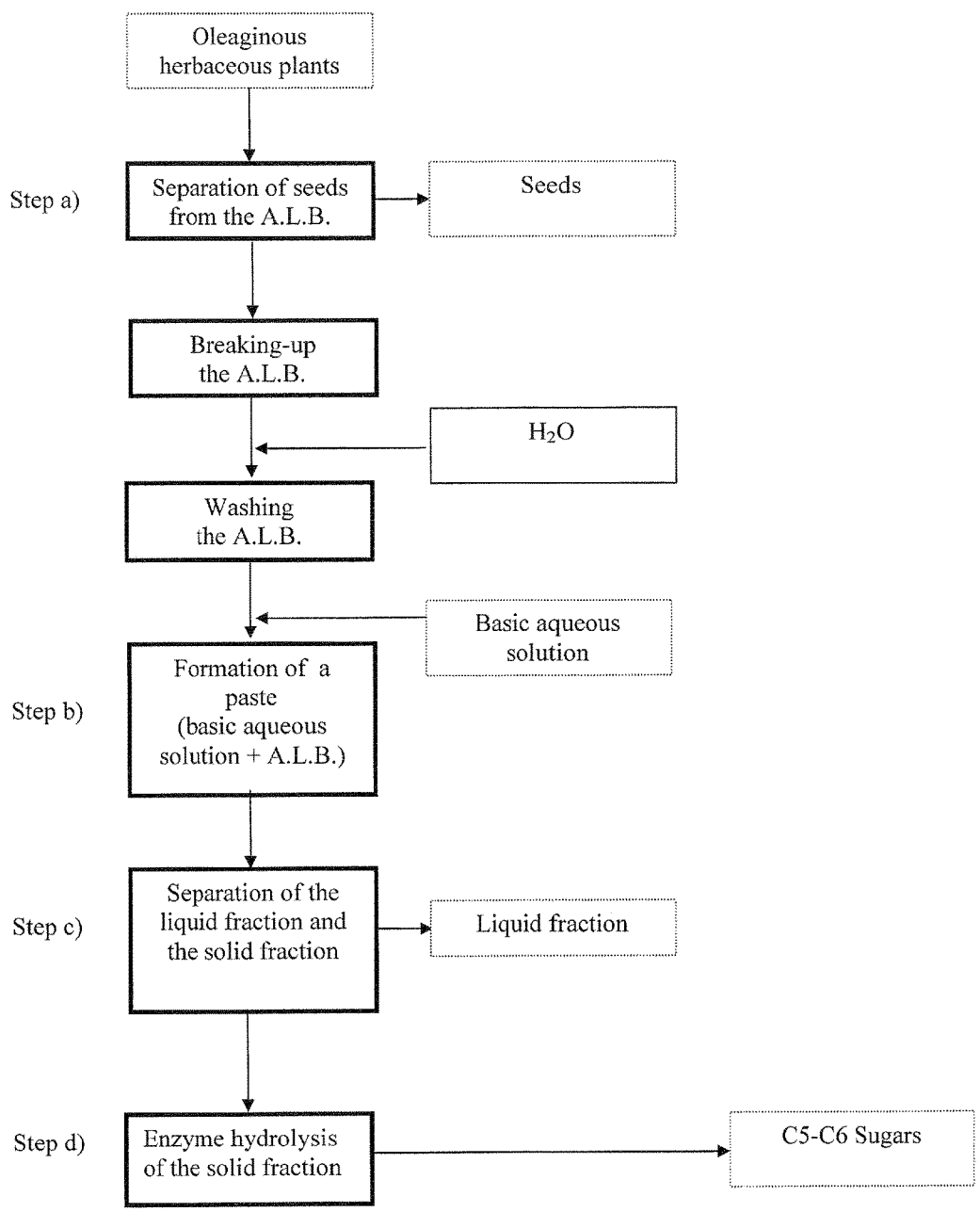
FIG. 2 is a flow diagram of a specific embodiment of the process of the present invention, comprising a washing step between steps a) and b).

FIG. 2 shows the flow diagram 2 of the process according to the invention comprising the optional washing with water after step a).

After step a), in the steps b) and c) of the process, the biomass is then submitted to mild chemical/physical treatment in order to remove lignin, extractables, ash and a limited quantity of hemicellulose and avoid the formation of degradation products such as for example furfural, HMF and their derivatives (such as formic acid and levulinic acid) and acetates, which inhibit subsequent sugar formation in step d).

In step b), the biomass will then be brought into contact with a basic aqueous solution at a temperature of between 10 and 95° C., preferably 25-95° C., more preferably 40-90° C., and subsequently subjected to separation, preferably by compression, in step c) of the process. The presence of an organic solvent is not required in the process of the invention. For environmental reasons, it is preferable that the basic aqueous solution contains 5 vol. % (i.e., volume of the organic solvent per total volume of the basic aqueous solution) or less of an organic solvent. Even more preferably, the solution is free of organic solvents.

In step c) of the process, the paste is separated into a solid phase mainly containing hemicellulose and cellulose and a liquid phase containing lignin and extractables. Said separation is performed by a device such as a press. In case a press is used in step c), the step of separation of the paste into a solid and a liquid phase is also referred to as "compression" or, alternatively, as "pressing".

The basic pH of the aqueous solution may be obtained by adding bases such as NaOH, LiOH, KOH, $Mg(OH)_2$, $Ca(OH)_2$, alkaline carbonates (e.g. $Na_2CO_3$, $Li_2CO_3$, $K_2CO_3$) and their mixtures. The use of NaOH, $Na_2CO_3$, and $K_2CO_3$ is preferred.

In case of using NaOH, in order to limit the overall cost of the process, this is added in a quantity preferably less than 10%, more preferably less than 8% and even more preferably less than 6% with respect to the weight of the biomass.

When using bases different from NaOH, amounts corresponding to the same NaOH equivalents, with respect to the weight of the biomass, are used.

The biomass is preferably impregnated with the said basic aqueous solution in step b) of the process according to the invention, forming a paste of a consistency such that it can be fed to the step c), with a solids concentration comprised from 10 to 50% by weight.

Step b) may take place under static conditions (i.e. without agitation) or preferably under gentle agitation, so as to obtain a paste having a homogeneous composition.

The paste obtained in step b) is then sent to the device (or "press") within which the separation process takes place (step c)). Preferably, said separation is performed by compression.

In a preferred embodiment of the process according to the invention, a part of the basic aqueous solution is added to the paste during the pressing in step c). By operating in this way it is possible to reduce the quantity of bases still further. This has clear advantages from the economic point of view and from the point of view of disposal of the bases in the form of salts.

The paste obtained in step b) can have a solid content ranging from 10 to 50% by weight, also depending on the way of performing the step c).

When the separation of the solid and liquid fractions is performed by using a device like a filter press, advantageously the paste is prepared in a single batch and has a solid content ranging from 10 to 25% by weight, preferably from 15 to 20% by weight.

When the separation of the solid and liquid fractions is performed by feeding the paste to a continuous press such as a system for crushing oleaginous seeds, advantageously the paste has a solid content ranging from 20 to 50% by weight, preferably from 25 to 40% by weight.

In case of using a continuous press, the steps b) and c) can be optionally performed in the same device by feeding to said continuous press the lignocellulose biomass and the basic solution separately.

The temperature during step c) is preferably less than 100° C., more preferably between 10 and 95° C., even more preferably 25° C. and 95° C. and still more preferably between 40 and 90° C.

The device capable of separating the solid fraction and a liquid fraction used in step c) is preferably a hydraulic or mechanical press. Preferred examples of presses are systems for crushing the oleaginous seeds, filter presses or any system used for the pressing of fibrous materials. The presses may comprise single shaft or dual shaft systems and may work continuously or discontinuously. Machines for crushing seeds which produce a further effect of defibering the biomass are particularly preferred.

Advantageously, the press used for pressing the seeds obtained in step a) may be used in step c) of the process. The press may be used individually or as part of a set.

Pressing is advantageously performed at temperatures between 25 and 100° C. These temperatures may be obtained either through the effect of friction within the press or through heating and thermostatting the press.

As a result of pressing, a solid fraction containing mainly cellulose and hemicellulose and a liquid fraction containing lignin, acetates, hemicellulose and other extractables are obtained.

In order to obtain an effect of concentrating the lignin in the liquid fraction and more efficient enzyme attack on the cellulose and hemicellulose, in a preferred embodiment of the invention, the solid fraction and the liquid fraction are fed to the press from which they have been obtained or to another press. The entire liquid fraction or part of it may be used. Water may be fed together with the solid fraction and the liquid fraction. This operation is advantageously repeated one or more times.

This means that according to a preferred embodiment, the solid fraction obtained in step c) is combined with at least one of water and a part or the entirety of the previously obtained liquid fraction, and the thus obtained paste is separated again into a solid fraction and a liquid fraction. It is preferable to combine the solid fraction at least with a part or the entirety of the liquid fraction and optionally add further water, if desired.

The procedure of combining and separation may be performed one or more times. The total number of these optional combining/separation steps is preferably within the range of 1 to 10, more preferably 2 to 6. The same type of device (e.g., a press) as used in step c) may be used for the separation. It is possible to use one single device, e.g., by feeding the paste back to the same device as used for step c) and/or the preceding combining/separation step, or a plurality of devices such as serially connected presses. For example, it is possible to use a system of presses in cascade, in which the solid fraction and the liquid fraction containing lignin, extractables, ash and acetates obtained in step c) and/or the preceding combining/separation step are fed to the subsequent combining/separation step until better availability for enzyme attack on the solid fraction is achieved.

By varying the conditions of solids concentration, temperature and composition of the aqueous solutions added at the various combining/separation (e.g., pressing) steps, it is also possible to selectively extract individual components of the biomass (i.e. lignin, acetates, ash, etc.) in the liquid fraction.

The liquid fractions obtained in the step c) and/or the subsequent combining/separation step(s) may be partly or wholly pooled.

The liquid fraction obtained after the separation (e.g., pressing) in step c) and/or the subsequent combining/separation step(s), which is rich in lignin, may be further treated chemically or physically and may be recycled as aqueous solution in the pre-treatment according to the invention, after the addition of a suitable quantity of base.

From this liquid fraction it is possible to obtain, for example after acidification and precipitation, lignins of high quality which can be used for the production of phenols, polyurethanes, reaction products with anhydrides and polyanhydrides. The lignins may also be used as fillers and reactive nano-fillers, for example in plastics materials, or as reinforcing additives for rubbers or for biodegradable polyesters. An example application of the polyesters obtained is the production of plant pots for nurseries.

Through methods known in the art, for example by adding a suitable quantity of acid and alcohols to the liquid fraction, it is also possible to facilitate precipitation and consequent recovery of carbohydrates, mainly comprising C5 sugars, which may be present therein.

The solid fraction obtained after pressing in step c) or any subsequent pressing steps has a water content which is typically less than 50% by weight, for example less than 40% by weight. This solid fraction is rich in carbohydrates (i.e. cellulose and hemicellulose) and, in case of processing of oleaginous herbaceous plants having not more than 20% by weight of lignin with respect to the dry weight of the above-ground lignocellulose biomass, has a lignin content of not more than 10% with respect to the dry weight of the biomass, determined as described above. A further advantage of the process of the present invention is that other contaminants such as for example furfural and HMF are not present in the solid fraction, or only present in a negligible amount. This allows to obtain in step d) C5-C6 sugars with reduced lignin and inhibitors content which are particularly suitable for fermentation processes and require simple operations for separating and purifying products after fermentation.

The solid fraction obtained after the completion of step c) and/or the optional combining/separation step(s) described above may optionally be subjected to one or more washing with water, or with a slightly acidic aqueous solution, to remove the residual base (step c-1)). The washing can be advantageously done by a counter-current extraction.

After the washing, the solid fraction obtained is submitted to enzyme hydrolysis in step d).

Figure 3:
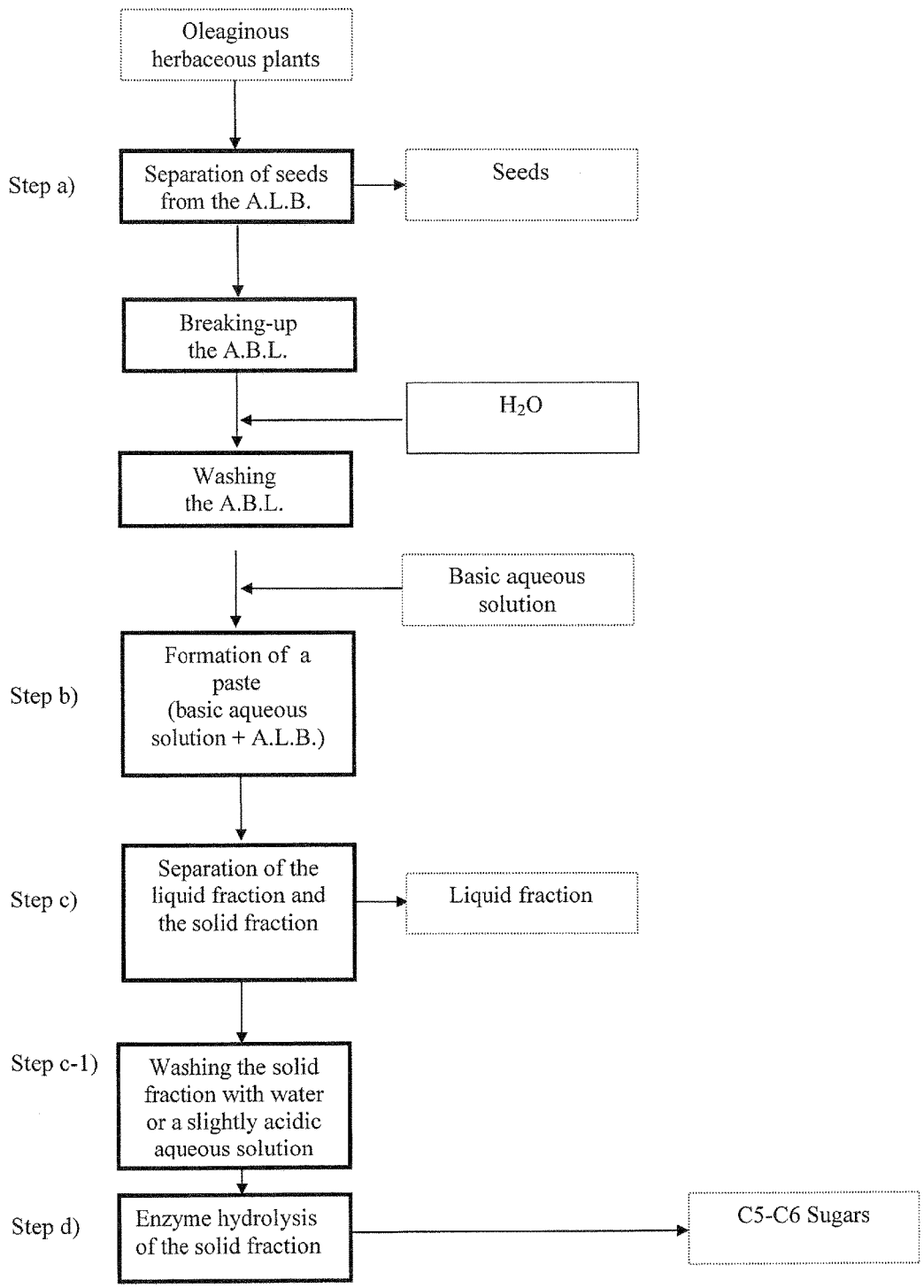
FIG. 3 is a flow diagram of another embodiment of the present invention, comprising a first washing step between steps a) and b) and a second washing step between steps c) and d).

FIG. 3 shows the flow diagram 3 of the process according to the invention comprising the optional washing with water in step a) and the optional washing of the solid fraction of step c-1).

In the process according to the invention, steps from a) to c-1) represent the so-called "pre-treatment".

The carbohydrate-rich solid fraction obtained after pre-treatment of the biomass is subjected to sugar-forming enzyme treatment to yield simple C5-C6 sugars in step d) of the process.

The enzyme treatment is performed using hydrolytic enzymes or their mixtures capable of splitting the carbohydrates to monosaccharides (e.g., cellulases and/or hemicellulases).

Step d) of enzyme hydrolysis may advantageously be performed according to the invention by feeding a solution containing the said enzymes and the solid fraction to a press through a process of continuous pressing/sugar formation.

As an alternative, this may be performed by mixing the solid fraction with the said enzymes in a batch reactor. Densifying additives which will correct the viscosity of the paste and reduce the crystallinity of the cellulose can be added at various steps in pressing and/or pressing/sugar formation.

The simple C5-C6 sugars obtained through the process according to the invention may therefore be subjected to conversion by chemical or biochemical means (e.g. fermentation) to obtain organic compounds.

Examples of biochemical processing are fermentation performed by bacteria (e.g. *E. coli*) or by oleaginous yeasts such as for example those belonging to the genera *Yarrowia, Candida, Rhodotorula, Rhodosporidium, Cryptococcus, Trichosporon* and *Lipomyces, Yarrowia* and *Candida* being particularly preferred.

Organic compounds which can be obtained through such treatments are for example dialcohols (preferably butandiol), monoalcohols, hydroxyacids and diacids, amino acids and diamines.

For example, mixtures of C5 and C6 sugars may be used by *E. coli* genetically modified by the process described in U.S. Pat. No. 8,067,214 B2 to obtain butandiol.

The sugars obtained may also be subjected to chemical conversion processes.

Examples of chemical conversion are the isomerisation of glucose to fructose and subsequent dehydration in an acid environment in order to obtain HMF, which can in turn be oxidised, yielding furan dicarboxylic acid and its derivatives.

Chemical intermediates which can be obtained via the conversion of sugars produced by the process according to the invention, such as for example butandiol, succinic acid, adipic acid, muconic acid, furandicarboxylic acid, terephthalic acid, levulinic acid, lactic acid and polyhydroxyalkanoates are useful as monomers for the synthesis of polymers, in particular polyesters.

In another embodiment of the process according to the invention, a fraction of the residual above-ground lignocellulose biomass is used to produce energy and/or biofuels through combustion/pyrolysis processes and/or biogas and/or hydrogen.

EXAMPLES

A non-limiting embodiment of the process according to the invention will now be described.

Example 1

A sample of *Cynara cardunculus* variety *altilis* was used.
Step a)
At the time of harvesting the seeds were separated from the remaining above-ground lignocellulose biomass comprising stems, leaves and capitula (without the seeds). The lignin content was approximately 18% with respect to the dry weight of the biomass. The biomass was then ground to a size of 1-3 mm in a mill of the Retsch M 100 type.
Step b)
100 g of biomass (having a moisture content of 10%) and 350 of distilled water were placed in a cylindrical reactor fitted with baffles and an alternating blade mechanical stirrer, thermometer, pH meter and dropping funnel.

The paste obtained was then raised to a temperature of 90° C. using a heating bath and a 12% solution of NaOH was added dropwise, keeping the pH at values below 11.

50 ml of solution corresponding to a total of 6 g of NaOH were added over 3 hours, obtaining a paste with 18% of biomass. Stirring was continued for a further 2 hours.

Step c)

The paste obtained during step b) was pressed using a laboratory filter press.

The resulting solid phase was then successively washed with water to neutral pH. After drying, 62 g of solid fraction were obtained.

The liquid fraction after pre-treatment was analysed and demonstrated a lignin extraction of approximately 70% and minimum hydrolysis of the hemicellulose, corresponding to a loss of 5% with respect to the initial hemicellulose content.

Step d)

The solid fraction obtained was then subjected to enzyme hydrolysis.

100 mg of solid fraction were added to 9.8 ml of acetate buffer (pH 4.8) in a flask and inoculated with 200 µl of Accellerase 1500 (an enzyme complex containing enzymes having a cellulolytic and hemicellulolytic activity). The flask was held at 50° C. for 48 hours.

The reaction mixture (comprising solid fraction, buffer and enzyme solution) was then centrifuged. The concentration of glucose in solution was then determined using a YSI 2900 biochemical analyser.

44.7 mg of glucose was obtained from enzyme hydrolysis of 100 mg of solid fraction treated according to the invention. The same quality of untreated biomass subjected to enzyme hydrolysis in the same way instead yielded 3.99 mg of glucose.

Example 2

Step a)

A sample of above-ground lignocellulose biomass of *Cynara cardunculus* analogous to that used in Example 1, was obtained by separation of the seeds at the time of harvesting, as in Example 1.

The biomass was then ground to a size of 1 mm in a mill of the Retsch M100 type.

Step b)

100 g of biomass (having a moisture content of 10%) was impregnated with 200 ml of aqueous solution containing 5 g of NaOH and homogenised in a mixer for 15 minutes at ambient temperature. The biomass easily absorbed the aqueous solution, acquiring the properties of a flowing moist powder, which could also be described as a paste and fed to the hopper of the press (biomass content of 30%).

Step c)

The paste was fed to a Kern Kraft Screw Press KK 8/2 seed press machine with a head heated to 90° C., at a rate of approximately 900 g/h. The machine was provided with a screw operating at a speed of 15 rpm. The outgoing material comprised a solid fraction and a liquid fraction which were collected separately.

The solid fraction collected was mixed back with the liquid fraction in order to obtain an effect of concentrating lignin in the liquid fraction and more effective enzyme attack on the cellulose and hemicellulose. The paste so obtained was fed to the same press.

This operation was repeated three times, obtaining 62 g of washed and dried solid phase at the end of the fifth pressing.

Step d)

A sample of the solid fraction, which was washed with distilled water and dried, was obtained after each pressing.

100 mg of each sample of solid fraction was then subjected to enzyme hydrolysis to obtain C5 and C6 sugars as in Example 1, step d).

At the end of the enzyme reaction, the reaction mixture, filtered and diluted 1:10 with a 0.005 N solution of $H_2SO_4$, was then analysed by HPLC to determine the concentration of C5 and C6 sugars.

An instrument equipped with a Refractive Index detector and a Rezex-ROA-Organic Acid H+ (8%)300×7.8 mm column was used under the following operating conditions:

Flow: 0.6 ml/min
Temperature: 65° C.
Eluent: 0.005 N aqueous solution of $H_2SO_4$ The table below shows the quantity of sugars obtained following enzyme hydrolysis of the solid fraction at the end of each pressing.

| Solid fraction sample (100 mg) | Glucose (C6) (mg) | Xylose (C5) (mg) |
|---|---|---|
| 1st pressing | 32.1 | 13.2 |
| 2nd pressing | 34.1 | 14.0 |
| 3rd pressing | 39.3 | 14.9 |
| 4th pressing | 45.4 | 17.2 |
| 5th pressing | 46.9 | 18.2 |

The example demonstrates that pre-treatment according to the invention is effective as regards lignin extraction, increasing the efficiency of enzyme hydrolysis, and preserves the hemicellulose in the solid fraction, providing high yields of C5 and C6 sugars.

Example 3

Step a)

A sample of above-ground lignocellulose biomass of *Cynara cardunculus* analogous to the one used in the previous Examples was obtained by separation of the seeds at the time of harvesting, as in Example 1.

The biomass was ground to a size of 1 mm in a mill of the Retsch M100 type. 100 g of biomass (having a moisture content of 10%) and 200 ml of water were then shaken in a mixer for 10 minutes at ambient temperature.

The paste so obtained was fed to a Kern Kraft Screw Press KK 8/2 seed press machine with a head heated at 100° C., at a rate of approximately 900 g/h. The machine was provided with a screw operating at a speed of 15 rpm. The outgoing material comprised 132 g of a wet solid fraction and 135 g of a brown liquid fraction which were collected separately. The analysis of the liquid fraction showed the presence of glucuronic, succinic, lactic, acetic and levulinic acids, for a total acidity corresponding to 0.8 g of NaOH.

Step b)

The wet solid fraction, corresponding to a dry weight of 73 g, was treated as in Example 2 with a solution of NaOH (4.5 g) in water (200 ml) and homogenised in a mixer for 15 minutes at ambient temperature.

Steps c) and d) were carried out as described in Example 2, obtaining at the end of the fifth pressing 46.7 mg of glucose and 18.5 mg of xylose.

Example 4

Step a)

A sample of above-ground lignocellulose biomass of *Cynara cardunculus* analogous to the one used in the previous Examples was obtained by separation of the seeds at the time of harvesting, as in Example 1. The biomass was ground to a size of about 5 mm in a mill of the Cumberland type.

Step b)

4.01 kg (10% humidity content) of lignocellulose biomass and a solution of 250 g of NaOH in 7.99 kg of water were stirred in a 50 liters mixer for 2 minutes at ambient temperature (12.3° C.).

Step c)

The paste obtained was fed to a continuous press for oil crushing of the MIG PC 25 type, having a capacity of 12 kg/h and equipped with a screw of 110 mm diameter and L/D=4.4, rotating at 10 rpm.

The solid and liquid fractions were separated affording 6 kg of extruded wet biomass (51.7% of solid) and 5.6 kg of a suspension (liquid+paste) to be added to the subsequent feeding.

Step d)

After washing with water in order to eliminate the residual base, the solid was submitted to enzyme hydrolysis affording 1.06 kg of sugars.

The invention claimed is:

1. A process for the production of fermentable C5-C6 sugars from oleaginous herbaceous plants belonging to the Cardueae tribe, comprising the steps of:
   a) mechanically separating the seeds from the above-ground lignocellulose biomass of the oleaginous herbaceous plants and comminuting said lignocellulose biomass;
   b) bringing the comminuted lignocellulose biomass into contact with a basic aqueous solution containing 5 vol. % or less of an organic solvent in order to prepare an aqueous paste containing the comminuted lignocellulose biomass in an amount of 10 to 50% by weight, at a temperature of between 10 and 95° C. and for a time of between 1 minute and 24 hours;
   c) separating the paste into a first solid fraction and a first liquid fraction;
   d) subjecting the solid fraction to enzyme hydrolysis of the hemicellulose and cellulose contained therein.

2. The process according to claim 1, further comprising after step a), extracting from the seeds an oil extract.

3. The process according to claim 1, wherein after step a) and before step b), said comminuted above-ground lignocellulose biomass is washed with water.

4. The process according to claim 1, wherein after step c) and before step d), the solid fraction is washed one or more times with water or with a slightly acidic aqueous solution.

5. The process according to claim 1, wherein the oleaginous herbaceous plants belong to the species *Cynara cardunculus* or *Silybum marianum*.

6. The process according to claim 1, wherein, after step c), the first solid fraction is combined with at least one selected from water and a part or the entirety of the previously obtained first liquid fraction to obtain a paste; and the thus obtained paste is separated into a second solid fraction and a second liquid fraction; said combining and separation being performed one or more times; and the finally obtained solid fraction is processed further according to step d).

7. The process according to claim 6, wherein the first solid fraction is combined with part or the entirety of the previously obtained first liquid fraction, optionally in combination with water.

8. The process according to claim 1, wherein the separation of the paste into a first solid fraction and a first liquid fraction is performed with a hydraulic or mechanical press or with a cascade of hydraulic or mechanical presses.

9. The process according to claim 1, wherein the said basic aqueous solution of step b) is obtained by adding a base selected from NaOH, LiOH, KOH, $Mg(OH)_2$, $Ca(OH)_2$, alkaline carbonates and their mixtures to water.

10. The process according to claim 9, wherein the base is NaOH and is added in a quantity of less than 10% with respect to the weight of the lignocellulose biomass.

11. The process according to claim 1, wherein the basic aqueous solution is free of organic solvent.

12. The process according to claim 1, wherein step c) is performed at a temperature below 100° C.

13. The process according to claim 12, wherein step c) is performed at a temperature between 25° C. and 95° C.

14. The process according to claim 1, wherein the lignocellulose biomass in step a) is comminuted to an average particle size of 2 cm or less.

15. The process according to claim 1, wherein step d) is performed with a mixture of cellulase and hemicellulase enzymes.

* * * * *

UNITED STATES PATENT AND TRADEMARK OFFICE
CERTIFICATE OF CORRECTION

PATENT NO. : 10,138,505 B2
APPLICATION NO. : 14/385823
DATED : November 27, 2018
INVENTOR(S) : Catia Bastioli et al.

Page 1 of 1

It is certified that error appears in the above-identified patent and that said Letters Patent is hereby corrected as shown below:

On the Title Page

Item (30), under "Foreign Application Priority Data,":
"Mar 20, 2012       (IT) .................... NO2012A0002"

Should read:
--Mar 20, 2012       (IT) .................... NO2012A000002--.

Signed and Sealed this
Fifth Day of March, 2019

Andrei Iancu
*Director of the United States Patent and Trademark Office*